United States Patent [19]

Cousin

[11] Patent Number: 4,928,702

[45] Date of Patent: May 29, 1990

[54] DEVICE FOR PICKING OFF AND EVALUATING A PRESSURE, IN PARTICULAR A PRESSURE OF A FLUID

[76] Inventor: Bernard M. Cousin, 37460 Montresor, France

[21] Appl. No.: 40,735

[22] Filed: Apr. 20, 1987

Related U.S. Application Data

[62] Division of Ser. No. 324,551, Nov. 24, 1981, abandoned.

[30] Foreign Application Priority Data

Dec. 5, 1980 [FR] France .................. 8025815
Jun. 25, 1981 [FR] France .................. 8112457

[51] Int. Cl.$^5$ ............................................. A61B 5/02
[52] U.S. Cl. ................................................ 128/678
[58] Field of Search .................. 128/687–690, 128/666, 677–680

[56] References Cited

U.S. PATENT DOCUMENTS

| | | | |
|---|---|---|---|
| 2,854,968 | 10/1958 | Wright | 128/690 |
| 3,701,283 | 10/1972 | Lichfield | 73/705 X |
| 3,704,708 | 12/1972 | Iberall | 128/666 X |
| 3,911,902 | 10/1975 | Delpy | 128/675 |
| 3,926,179 | 12/1975 | Petzke et al. | 128/672 |
| 4,210,029 | 7/1980 | Porter | 128/748 X |

FOREIGN PATENT DOCUMENTS

525375  5/1955  Italy ........................ 73/705
125681  7/1959  U.S.S.R. ..................... 128/748

OTHER PUBLICATIONS

Taylor, W. B. et al, "A High Resolution Transrectal UTS System", UTS in Med & Biol., vol. 5, 1979, pp. 129–138.

*Primary Examiner*—Francis Jaworski
*Attorney, Agent, or Firm*—Lane & Aitken

[57] ABSTRACT

The invention relates to a device for picking off a pressure, particularly of a fluid, and to utilize it either for measuring or for transcodable signals.

It comprises a capsule 1 which is provided with an opening 2 and which is closed by a flexible membrane 4, accessible to the pressure to be picked off, with said capsule 1 containing a non-compressible liquid 5.

It is characterized in that it comprises compressible elastic means, positioned opposite the opening 2 and exerting a calibrated and invariable counter pressure on the non-compressible liquid 5 to assure the automatic and instantaneous returning of the flexible membrane 4 which closes the opening 2.

The elastic compressible means can be formed by an air pocket 7 which may be separated from the opaque non-compressible liquid 5 by a non-compressible transparent liquid 23.

The device is especially adapted to the measuring of arterial blood pressure.

17 Claims, 5 Drawing Sheets

DEVICE FOR PICKING OFF AND EVALUATING A PRESSURE, IN PARTICULAR A PRESSURE OF A FLUID

This is a division of application Serial No. 324,551, filed November 24, 1981, now abandoned.

This invention relates to a device for picking off and evaluating a pressure, in particular a pressure of a fluid

BACKGROUND OF THE INVENTION

There are many cases where it is necessary to pick off a pressure, particularly of a fluid, and to utilize it either for measuring or for generating encodable signals.

For example, sound is produced the grooves of a record, which react to the variable pressure, applied to the grooves a reading head; atmospheric pressure is measured by of barometers and altimeters weight is measured by; the pressure of a body placed on a scale; the blood pressure in the arteries of a living body is measured for gaining medical information etc.

Among the numerous cases of pressure detection there if one which is particularly important and that is detection of anterial pressure. As a matter of fact, when an operation on the human body is to be carried out, not only physiological data are taken into account but also psychological factors concerning especially the possibility of pain which such measuring can cause.

Up to now the most common means for blood pressure detecting has been the one in which the artery to be examined is cut off completely with the help of an inflatable sleeve or garrote. It is clear that such a means only allows the measuring of blood pressure in some parts of the body.

Other means of picking off pressure have therefore been devised, like the one described in U.S. Pat. No. 3,704,708.

However, this disclosure is different from the present invention.

As a matter of fact, U.S. Pat. NO. 3,704,708 is based on the principle that the device does not depend on the condition of the vascular system but only on the true transmission of a hydrostatic pressure (col. 4, lines 33 to 37 and col. 7, lines 5 to 10).

The functioning of the device requires that the examined artery be flattened (col. 4, lines 40 and 41) and needs the presence of a skeletal bone (col. 3, lines 44 and 45).

For this reason the capillary tube 110 is provided with a movable stopper 125 (col 6, line 48), by means of which it can be temporarily closed (col. 6, lines 66 and 67).

The stopper 124 is replaced after the liquid 126 (which is subjected to atmospheric pressure) rises, so that there is no counter pressure at all. If the stopper 124 is replaced before rising of the liquid, the counter pressure from the captured air has an unknown value which varies upon each measurement since the volume of air is variable (the liquid 126 rises more or less when the stopper 124 is replaced).

BROAD STATEMENT OF THE INVENTION

In contradistinction to the disclosure described above, the present invention allows the measuring of the elasticity of the examined blood vessel, the speed of propagation of the blood pressure wave and the pressure of the artery in those areas which are as critical as the center of the retina or the carotid artery. This is due to the fact that the examined blood vessel is not compressed but that the device is merely placed onto a pulse.

The present invention therefore provides a novel solution for the problems of measuring a pressure and uses simple and efficient means.

BRIEF DESCRIPTION OF THE DRAWINGS

The invention will be better understood by reading the following detailed description in which reference is made to the attached drawings. It is to be understood that the description and the drawings set forth only examples, but are not limited thereto.

DETAILED DESCRIPTION

Figure 1:
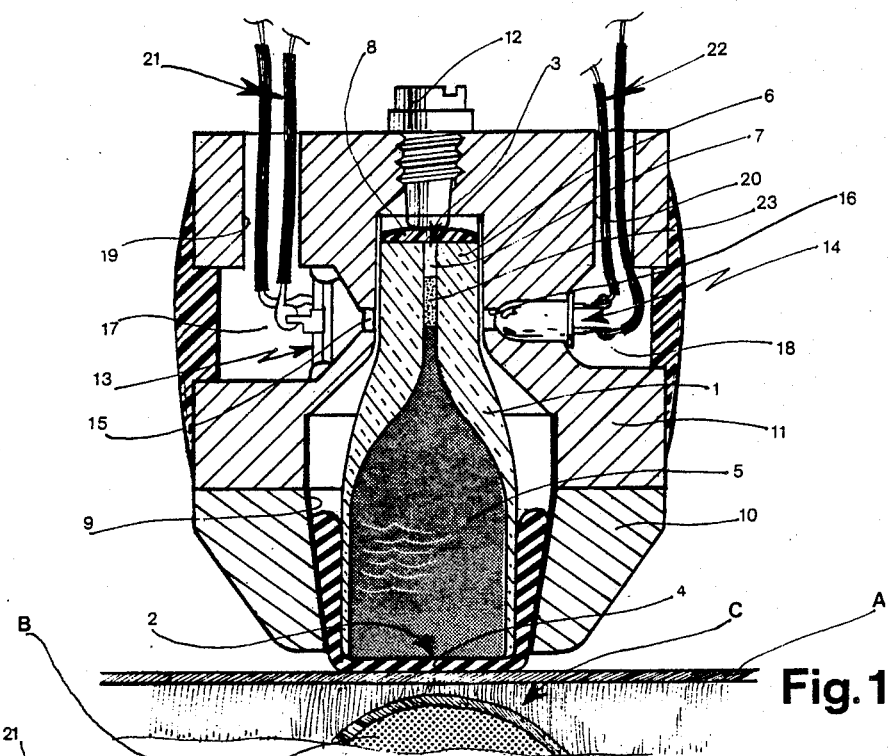
FIGS. 1 and 2 are two partial schematic sections of a device according to the invention showing a first embodiment thereof.
Figures 2, 3:
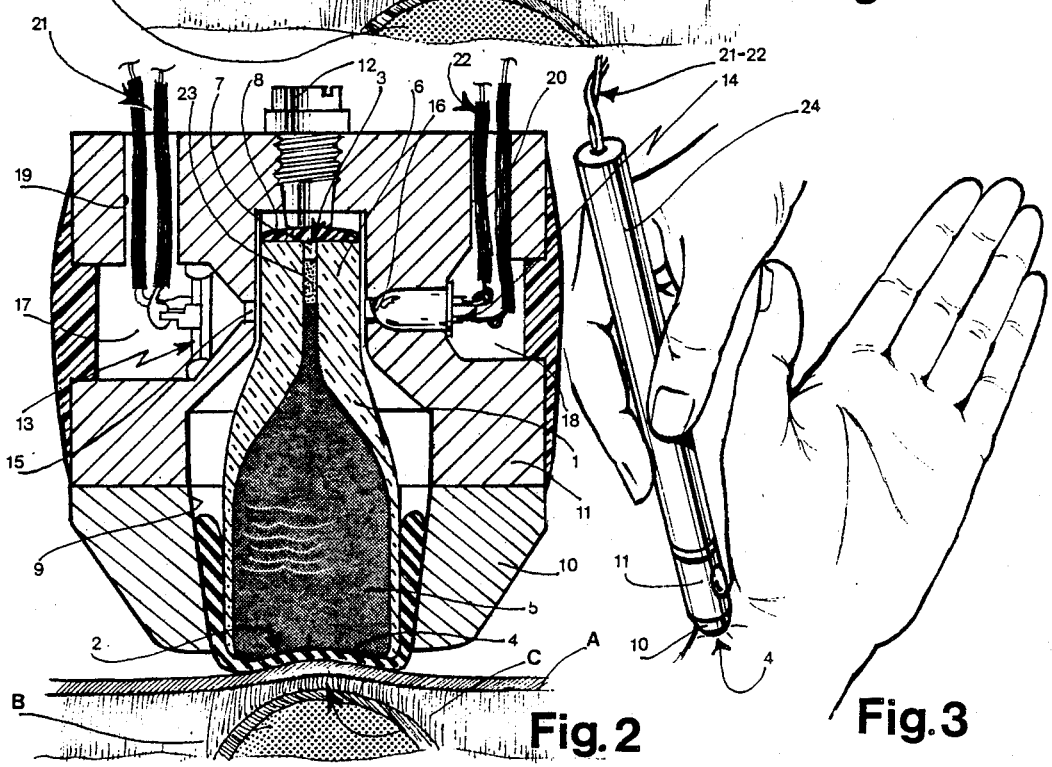
FIG. 3 is a schematic view which illustrates an example of an embodiment of the entire apparatus comprising a device according to the invention.

Referring to FIG. 1 and 2, it can be seen that the device according to the invention is intended for picking off a pressure, especially of a fluid, and to utilize it either for measuring or for generating encodable signals, and comprises a capsule 1 which has an opening 2 covered by a flexible membrane 4 which is accessible to the pressure to be picked off and which contains at least one non-compressible liquid 5. It further comprises compressible elastic means 7 situated opposite the opening 2 which exerts a calibrated and invariable counter pressure on the non-compressible liquid 5 so as to assure the automatic and instantaneous returning of the flexible membrane 4 to its rest position.

According to the embodiment shown, there is another opening 3 opposite the opening 2 which is smaller than the opening 2 and which is provided with a permanent closing means 8 which cannot be removed in normal use.

In addition, the portion of the capsule 1 opposite the opening 2 is formed into a neck 6.

According to the embodiment which is shown in FIGS. 1 and 2, the compressible elastic means are constituted by the combination of a gas like air 7 placed in the capsule 1 and a rigid closing means 8 which cannot be removed in normal use.

It can thus be seen that by subjecting the membrane 4 to the pressure to be measured and by holding the capsule 1 in such a manner that it remains immobile, the pressure will deform the membrane 4 and cause a decrease in the inside volume of the capsule 1. As a consequence the non-compressible liquid 5 will rise in the neck 6.

The displaced volume in the large zone of the capsule 1 by necessity is the same as the one which is displaced in the neck 6; but since the latter is much narrower, it is clear that the degree of movement of the liquid 5 in the neck is considerably greater than that of the membrane 4.

The result is that a very small displacement of the membrane 4 leads to a considerably greater displacement of the liquid 5 inside the neck 6. This allows very precise measuring by reliably determining the level of the liquid 5.

In order to be able to determine not only a given pressure but also instantaneous variations of this pressure, it is indispensible that the non-compressible liquid 5 is subjected to a calibrated counter pressure which assures the automatic returning of the membrane 4.

FIGS. 1 and 2 show how this result is obtained, that is by providing a small volume of air 7 which is captured between the non-compressible liquid 5 and the stopper 8 which is, for example, made from a casting of a synthetic material.

Thus, the displacement of the non-compressible liquid 5 has the effect of compressing the air 7 against the closing means 8, while the relaxing of the membrane 4 is automatically followed by an expansion of the compressed air 7.

A device according to the invention can be attained by placing the capsule 1, filled and closed, into an opening 9, which is shaped generally like a truncated cone, formed in a support 10, thereby capping the unit by means of a body 11. The body is open at its center to receive the upper portion of the capsule 1, which fixed in position by means of a screw 12 having a flat end engaging the closing means 8.

According to a feature of the invention, the device comprises a detector of the level of the non-compressible liquid.

According to a special embodiment the detector is of the optical type and is positioned adjacent to the capsule 1.

According to a modification, the capsule 1 is transparent and the non-compressible liquid 5 is opaque.

In the embodiment of FIGS. 1 and 2 the detector comprises an electric photocell 13 and a projector 14 - unit whose light axis of which is transverse to the one of the capsule 1.

In practice, this detector is implemented by providing two transversely alined apertures 15 and 16 which communicate with respectively larger seats 17 and 18 for the cells 13 and the projector 14, respectively.

The passages 19 and 20 for the electric wires 21 and 22 communicate with the seats 17 and 18.

The operation of the detector is well known. By supplying the light bulb of the projector 14 with an electric current which flows through the wires 22, the projector 14 is caused to emit a light beam which traverses the passage 16, the transparent material which constitutes the capsule 1, and the passage 15 to reach the photoelectric cell 13, which sends through its wires 21 an electric current proportional to the illumination which it receives from the beam emitted by the projector 14.

As long as the opaque and non-compressible liquid 5 has its upper level below the light beam, the electric current coming from the cell 13 will indicate an absence of pressure. When the level of the liquid 5 reaches the electric beam, the current generated by the cell 13 has a different value. The current may be applied to an apparatus for indicating the pressure on a display screen. The apparatus indication may either be the simple indication of the existence of pressure or an exact indication of said pressure by establishing a ratio between its value and the portion of the light beam which is darkened by the opaque liquid 5.

Because the level of the liquid undergoes relatively large displacement compared to the very small displacement of the membrane 4, the displacement is easy to detect and to obtain therefrom information in the form of very precise electric pulses.

FIGS. 1 and 2 show that the capsule 1 contains a noncompressible opaque liquid 5 and a non-compressible transparent liquid 23. These liquids do not mix so that a clear and contrasting contact line is established which constitutes the level to be detected.

In this manner possible reading errors are avoided because the very large difference in kind between the non-compressible liquid 5 and the air 7.

It has been chosen to illustrate the invention by means of a device adapted for measuring blood pressure in an artery. Such a device is shown in FIG. 3 where the inventive means as such (as shown in FIGS. 1 and 2) can be connected with a body 24 fastened to the piece 11 in such a manner that the user can handle the complete apparatus like a pencil.

The invention is particularly interesting for this application since devices with inflatable sleeves do not allow taking the blood pressure in arteries like the carotid artery, the abdominal aorta, the central artery of the retina and many others because they are often. in areas where it is impossible to place the garotte which constitutes the inflatable sleeve.

In addition, measuring arterial blood pressure cannot be carried out continuously and requires the intervention of a practitioner.

Prior to the invention it was not possible to measure arterial elasticity or the speed of propagation of the wave of blood pressure, as is possible with a device according to the invention.

It is, of course, also possible to reach the blood directly, but this can only be done when the subject is operated on. Even, this method does not allow the examination of all the arteries pulse by pulse.

The device of the invention is based on the principle of converting purely mechanical information of the membrane 4 into electrical information, which can be evaluated by means of any suitable known apparatus.

It is thus possible to obtain a curve, provide a permanent display on a screen, place data in storage or provide an informative evaluation, either independently or in association with additional devices, such as cardiac stimulators, alarm systems etc.

It will be apparent that with the invention it is possible to measure the arterial pressure by putting the membrane 4 on any pulse including the pulses in areas not accessible by a garrote.

The device indicates the pressures exerted upon the membrane 4 which is brought in contact with the skin A. The displacement of the membrane 4 will be less than the displacement of the same surface of the wall of the artery B when the latter is not subjected to the device, because some of the displacement absorbed by the intermediate tissue B subjected to the pressure.

The increase in volume of the arterial segment B upon passage of the blood pressure wave must receive the opposing action of the counter pressure created in the device and not the reaction of the artery wall B.

The increase in volume of the segment B can be easily measured, since the reference used is the displacement of the upper level of the non-compressible liquid 5, which displacement is much greater than that of the artery B at equal pressure.

To make the pressure measurements, one can either hold the device as shown in FIG. 3, i.e. for a short time, or use means, such as nonelastic bracelets to rigidly hold the device in position.

By not associating the device with a body 24 in form of a pencil, but rather with a low base, it is possible to attach the device to the desired spot for relatively long periods, for example for several days or nights of intensive observation, as may be justified by the poor condition of the patient.

It is also possible to place several devices on spots which are most important, for example prior to an operation or in the case of urgent examinations.

It has been indicated above that it is practical to associate two liquids 5 and 23, both non-compressible and non-mixable, but with one being opaque and the other transparaent. As examples mercury may be the opaque liquid and glycerine the transparent liquid.

According to another embodiment of the invention, the capsule 1 is of a non-polished material and contains a liquid which renders it transparent at least in the area where the liquid is in contact with said capsule 1.

In this manner, the displacement of the liquid corresponds to the creation of a screen for the light beam from the photo-electric cell.

According to a special embodiment of the invention, the compressible elastic means are formed by a membrane 29 which may be associated with a spring 31.

Figure 4:
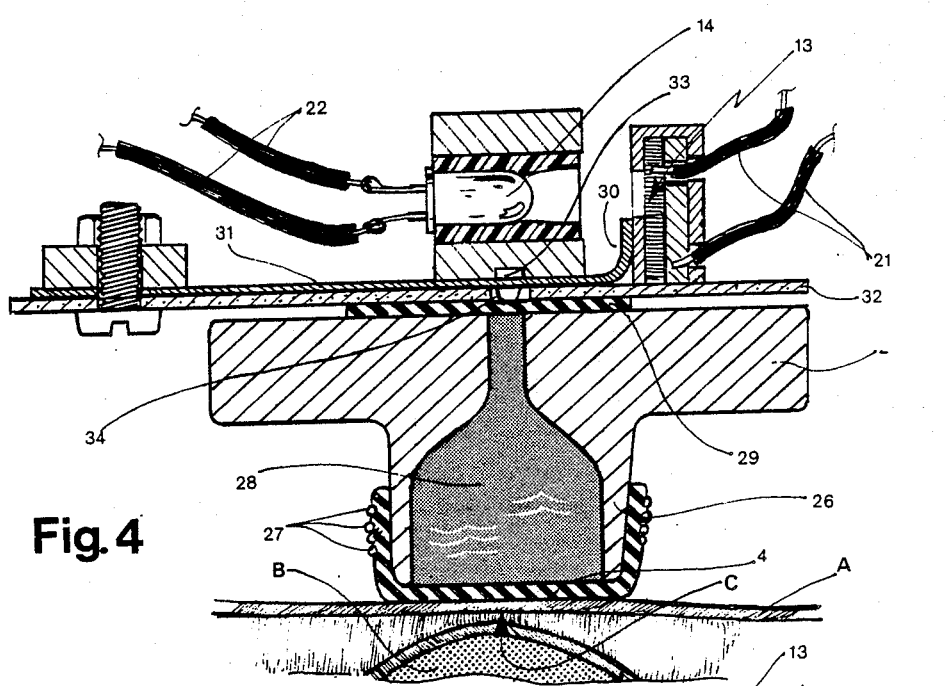
FIGS. 4 and 5 are two sectional schematic views of a second embodiment of the invention.
Figure 5:
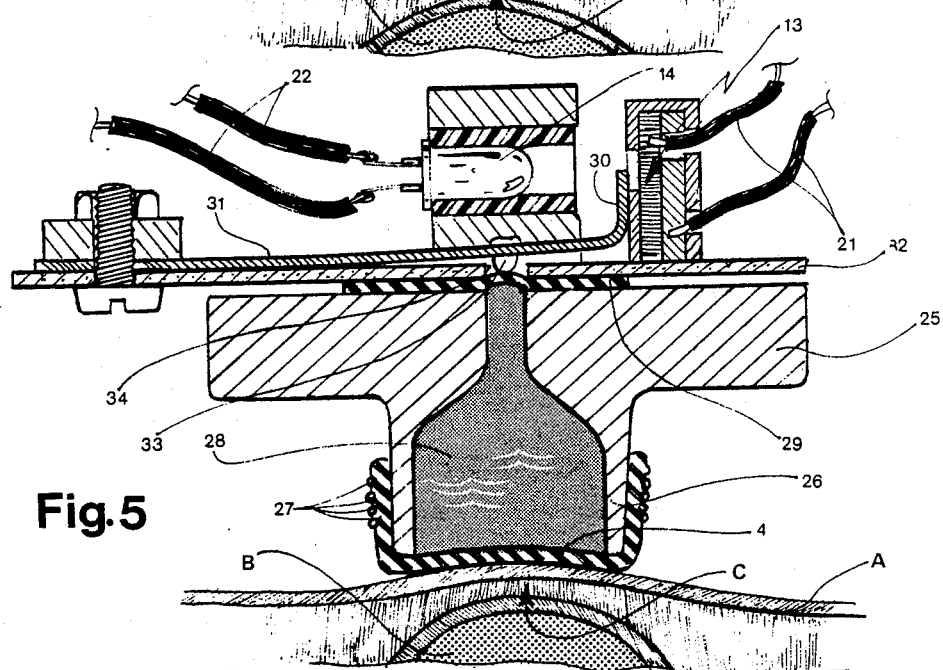

FIGS. 4 and 5 show such an embodiment.

It can be seen that here the capsule is not in the form of an independent container placed inside a support, but is created by a cavity conveniently formed at the inside of a piece 25 which has a mouth 26 on which the membrane 4 is kept by means of bands 27 which surround the unit.

The cavity or capsule is entirely filled with a non-compressible liquid 28 and the small opening is closed by an elastic membrane 29.

It is seen that in this embodiment the detector is formed by an electric photocell 13 and a light beam projector 14 the light axis of which is transverse to a movable screen 30, connected cinematically to an elastic membrane 29 which closes the small opening of the capsule, entirely filled by at least one non-compressible liquid 28.

According to a modification, the screen 30 is formed by a bent end of an elastic blade 31, fastened at its other end to a fixed portion 32 and provided with a stud 33, which is urged against the outer face of the membrane 29 by the elastic blade 31.

The fixed portion 32 is connected by any known means to the piece 25 and is traversed by an aperture 34 in which the stud 33 moves freely.

It is obvious that with this arrangement the small displacements of the membrane 4 cause greater displacements of the membrane 29 which pushes the stud 33 back and, consequently, the blade 31 and the screen 30, now being placed more or less completely in line with the light beam to black out at least a portion from which results a variable current in the wires 21.

When the membrane 4 receives a low pressure or zero pressure, the non-compressible liquid 28 and the elastic membrane 29 return to their normal position under the effect of the stud 33 which is pushed by the elastic blade 31, with this unit creating the desired counter pressure at a known value.

This arrangement can be adopted for reasons of space or needs of assembling. It has the advantage of greater resistance to shock since the action of the elastic blade 31 is more constant than that of the air bubble provided in the embodiment according to FIGS. 1 and 2.

Another advantage of this arrangement results from the fact that the device has complete stability in case of heat since the elastic blade 31 is practically completely unaffected by variations in temperature, while the air bubble can expand more or less according to the temperature which surrounds the device. This change can lead to slight variations in the value of the counter pressure.

According to another embodiment of the invention, no optical deflector is used, but the capsule is provided inside with at least two contacts, connected outside to an electric circuit and containing at least one non-compressible and electrically conducting liquid so that an electric connections established between the two contacts.

The electric circuit may comprise a resistance which varies according to the contacts which the conducting liquid engages.

It is also possible to provide electrodes which the conducting liquid covers to a greater or lesser degree to create variable electrical signals as a function of the pressure received by the membrane 4.

When an optical detector with phote-electric cells is used, the projector 14 can be eliminated to decrease the consumption of electric current by using the ambient light. In this case two photo-electric cells are placed in a position where they both receive the ambient light, but one of them is associated with a screen of the type 30 in such a manner that the one which receives the direct ambient light without being influenced by the device, serves as a reference to the one which is associated with the screen.

In order to measure the displacement of an arterial wall for calculating a value of arterial elasticity, a device according to the invention of one of the described types must offer a counter pressure (by air, a membrane or an elastic blade) which is smaller than the counter pressure exerted by the arterial wall. In FIG. 3 the displacement of the membrane 4 is therefore equal to the displacement of the same surface of the wall of the artery B minus the displacement absorbed by the intermediate tissue C. The apparatus thus indicates an amplified displacement. The ratio between this displacement of a surface and the pressure variation on that same surface gives the elasticity value of the artery.

Figure 6:
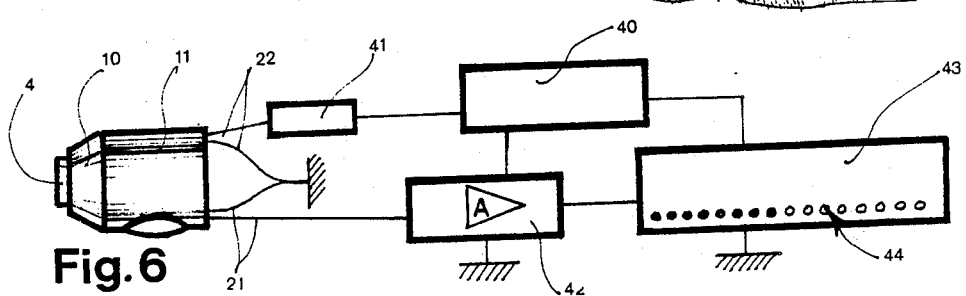
FIG. 6 is a schematic illustration showing the association of a device according to the invention with means for utilizing the information obtained by the inventive device.

FIG. 6 shows an example of the association between a portable device according to the invention and a fixed apparatus.

It can be seen in this figure that the unit of this installation comprises a supply system 40 of electric current, preferably of low voltage like 12 volts, a rectifier 41 at the input of the projector, an amplifier 42 at the output of the photo-electric cell and, finally, a display device 43, comprising here a series of light indicator openings 44, the lighting up or turning off of which is controlled by the amplified signal of the photoelectric cell, which signal is created by the movement of the membrane 4.

The above description shows that a device according to the invention allows the transformation of mechanical pulses into electrical signals, resulting from a pressure which varies more or less rapidly.

The invention has numerous applications and, as needed, the two essential components which are the volume displacement on the one hand and the counter pressure on the other hand, can be easily varied.

One can, for example, apply the invention to barometers, altimeters or tachometers (according to the principle of the Pitot tube in which the lateral counter pressure of fluid flow is used) and to all calibrated systems of liquids.

One can use a rigid intermediate plate for creating a balance.

By associating a movable mass with the membrane 4, the acceleration or deceleration to which the device is subjected can be measured.

The materials used allow the maximum reduction of the non-compressible liquid inertia in such a way that the invention can be applied to the manufacturing of reading heads for turntables or of microphones, in which connection it is pointed out that one can shape the device in accordance with the application.

It is also possible to apply the invention to the balance principle for the surveillance and care of plants in a container: when the humidity of the earth decreases, the pressure exerted upon the membrane of the device fixed under the container decreases and it can be provided that when a certain level on the device is reached, it causes the opening of an electric gate valve which feeds water into the container.

It is further possible to study the propagation of a pressure wave in a blower by arranging in line a series of devices and registering, simultaneously, the value given by each of the devices in such a way that one obtains at the same time the pressure and speed of the propagation of the wave.

According to a special embodiment, the compressible elastic means are associated with an element of transducing the mechanical information transmitted by said means into usable information such as electrical, electronic or similar signals.

The embodiment shown in FIGS. 4 and 5 can, for example, comprise, instead of an optical unit and a movable screen, a piezo-resistant plate (not shown) which is applied against the membrane 29 so as to transform the absolute pressures or differentials transmitted to the plate by the membrane 29 into electrical signals. Any other transducer element which is sensitive to pressures and/or movements of elastic compressible means can be utilized according to the given case. These elements can be freely chosen by anyone skilled in the art (variations of capacities, in magnetic fields etc.).

When the device is used for measuring blood pressure, a sufficient miniaturization can be sought for inserting it into the body. One can, in particular, place it in the cardiac region against one side which immobilizes it.

In this case solutions must be found for decreasing the size of the device and the strains imposed upon it, One can, for example, utilize an internal unit comprising, on the one hand, a "collector" comprising the capsule and its membrane and, on the other hand, two optical fibers ending at an external reading apparatus (projector and photo-electrical cell).

In order to eliminate the electric connecting wires, a miniaturized radio transmitter can be implanted with the collector and an outside receiver associated with any desired apparatus: display, alarm, information etc.

In the embodiment which was just described the compressible elastic means are formed of an elastic membrane which must be deformable to a rather large extend since the very design of this device provides that the non-compressible liquid is displaced to a greater height with respect to the membrane than at the input of the capsule where another membrane is provided which is subjected directly to the pressure to be measured.

In practice, it may be difficult to find a material which fulfills at the same time the function of the counter pressure, the function of tightness and the function of great displacement.

One is confronted, in effect, with conflicting demands as to elasticity, resistance etc.

Thanks to the embodiments which will now be described in connection with FIGS. 7 to 10, these problems are efficiently resolved.

Figure 7:
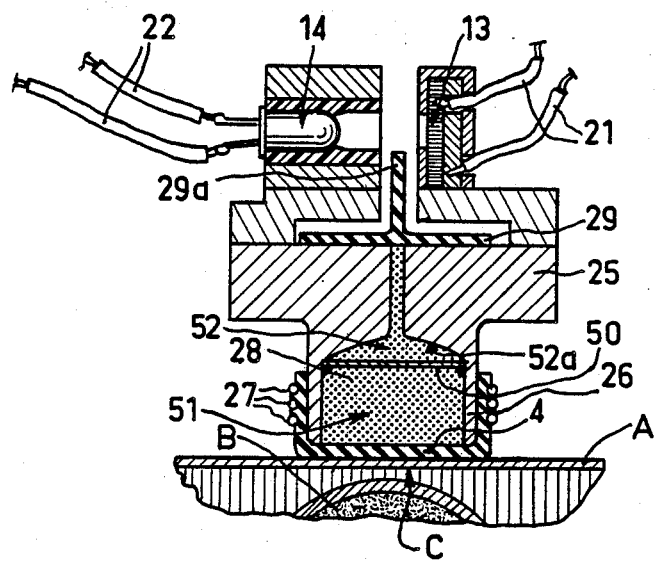
FIGS. 7 and 8 are two schematic sectional views of a device according to the invention in the two positions which correspond, respectively, to the picking off of a zero pressure and a positive pressure.
Figure 8:
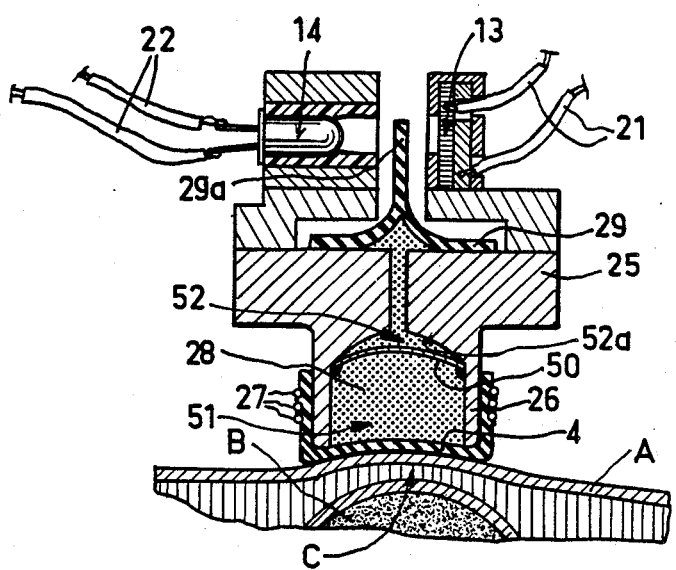

Referring to FIGS. 7 and 8, one can see a device according to the invention in the form of an embodiment in which the body 25 has a mouth 26 on which the membrane 4 is maintained by means of bands which surround the unit.

However, it is also possible to use the embodiment of FIGS. 1 to 3, in which a capsule 1, associated with a support 19–11 (FIGS. 1 to 3), is utilized.

Here the capsule (or the cavity provided inside the piece 25) contains a transverse deformable membrane 50, fixed at its periphery, and which determines two isolated chambers 51 and 52, one of which, 51, having the greater opening 2, is filled with a non-compressible liquid, and the other, 52, having the smaller opening 3, is filled with a non-compressible liquid, and, if required, by a gas like air 7.

With this arrangement it can be seen, especially when considering FIG. 8, that the deformation of the membrane 4 causes the deformation of the transverse membrane 50, and it is this one which assures the functioning of the counter pressure.

On the other hand, the displacement of the non-compressible liquid in the chamber 52 has the effect of lifting the membrane 29, and this lifting can be evaluated by the different means set forth above.

Thanks to these arrangements the membrane 29 can be made of a material which assures as reliably as possible the function of tightness and the function of lifting, independently of the function of counter pressure.

In other words, the function of counter pressure (or "calibrating") and the function tightness/displacement are disassociated.

The first function is assured by the membrane 50 which can be of metal, synthetic material etc., whereas the second function is assured by the membrane 29.

It is to be noted that the material of the membrane 50 can be chosen independently of the ratio of diameter to flexibility.

Thus, one can provide a membrane 50 of metal of large diameter to have a correct bending at the time of deformation due to the amount of pressure and a small, very flexible membrane 29.

To form the membrane 50, one can, for examble, utilize a sheet of foil with a thickness of 0.06 mm for a diameter if six mm which achieves exactly the desired bending for displacing in the chamber 52 a sufficient volume of non-compressible liquid.

It can be noted in FIGS. 7 and 8 that for measuring the pressure, the combination of a photo-electric cell 13 and a projector 14 has been chosen, between which a transverse screen 29a is provided. The screen 29a is fabricated in one piece with the membrane 29.

The functioning of this device is in all points identical to the one which has been described above.

Figure 9:
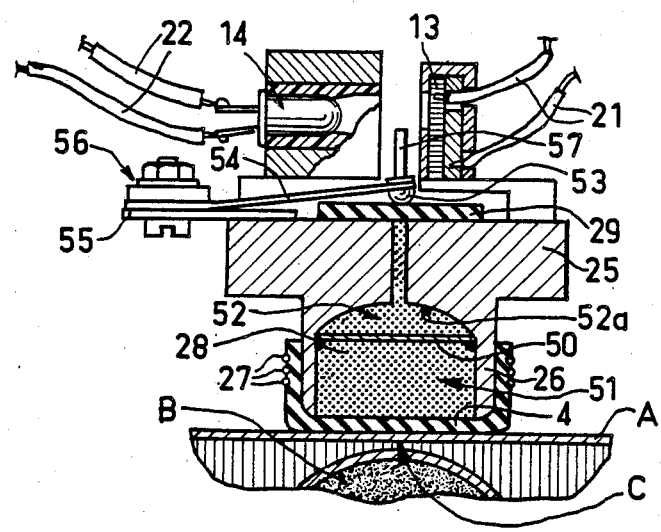
FIG. 9 is a schematic sectional view of another embodiment of the invention.

Referring now to FIG. 9, another embodiment can be seen according to which the membrane 29 is flat, i.e. in that it does not comprise the screen 29a. It receives at its center a stud 53, moved back by a spring blade 54, held against a fixed portion 55 by means of a screw - nut - assembly 56 and on which a screen 57 is arranged.

When the membrane 29 is lifted by the displacement of the non-compressible liquid in the upper chamber 52, the screen 57 is interposed between the light beam of the projector 14 and the photo-electric cell 13, as has been described above. When the non-compressible liquid enters again into the chamber 52, the membrane 29 returns to its original position due to its elasticity, whereas the screen 57 and the stud 53 are reset by the restoring resiliency of the blade 54.

According to one feature of the invention, the chamber 52 which has the smaller opening 3 at the curved wall 52a has a form equivalent to the one which the transverse membrane 50 can assume when it is maximally deformed, so that the membrane 50 can engage the curved wall 52a which serves as its stop.

According to a modification, the curved wall 52a of the chamber 52 has the shape of a spherical cap.

These arrangements are particularly visible in FIG. 8 in which a membrane 50 is shown which has been deformed by the effect of a pressure against the membrane 4.

It can be seen that the membrane 50 is close to the wall 52a and has a somewhat smaller curvature.

This indicates that the pressure exerted upon the membrane 4 is smaller than a pre-established maximum which has been calculated as a function of the capacity of deformation of the membrane 50.

When, on the contrary, the membrane 4 was subjected (accidentally or not) to an excessive pressure with respect to the elasticity of the membrane 50, the latter would be forcefully deformed but would be pressed against the wall 52a and therefore would be kept intact instead of being ruptured or separated from the shoulder of the piece 25 to which it is normally fastened.

These arrangements constitute a safety measure which protects the device against abnormal use or an accident which can happen if, upon letting the device fall, it hits the ground with its membrane 4.

It is obvious that the invention also allows a choice of diameters for the membrane 50 which is subject to only one value, i.e. the degree of the bend to be obtained.

Figure 10:
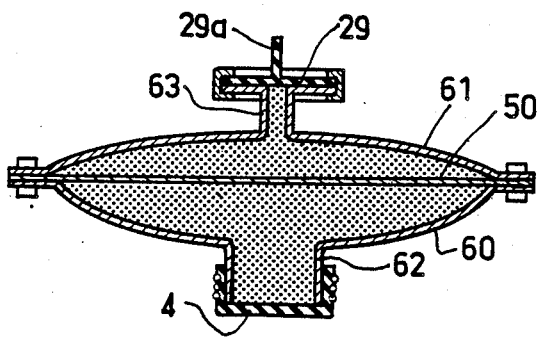
FIG. 10 is a schematic sectional view of still another embodiment of the invention.

In FIG. 10 a device according to the invention is shown whose proportions are deliberately exaggerated but which show the complete independence which exists between the diameter of the membrane 4, the diameter of the membrane 50 and the diameter of the membrane 29.

The device is obtained by assembling two half shells 60 and 61, each of which having a neck 62 and 63, respectively, of different diameters.

The upper shell 61 has the form of a spherical cap which serves as a stop for the membrane 50 as has been explained above.

With such a device a considerable amplification of the linear displacement between its origin on the level of the membrane 4 and its point of application on the level of the membrane 29 is attained.

Such an embodiment which comprises a membrane 50 of a very large diameter relative to the one of the other membranes, is interesting when one must choose to make this membrane 50 of a material of relatively low elasticity which only allows a very weak bend, which requires, for the purpose of compensating for this weakness, the providing of a great diameter so that the spherical cap created by the deformation of the membrane 50 is of a sufficient volume to give a significant linear displacement to the level of the membrane 29.

Figure 11:
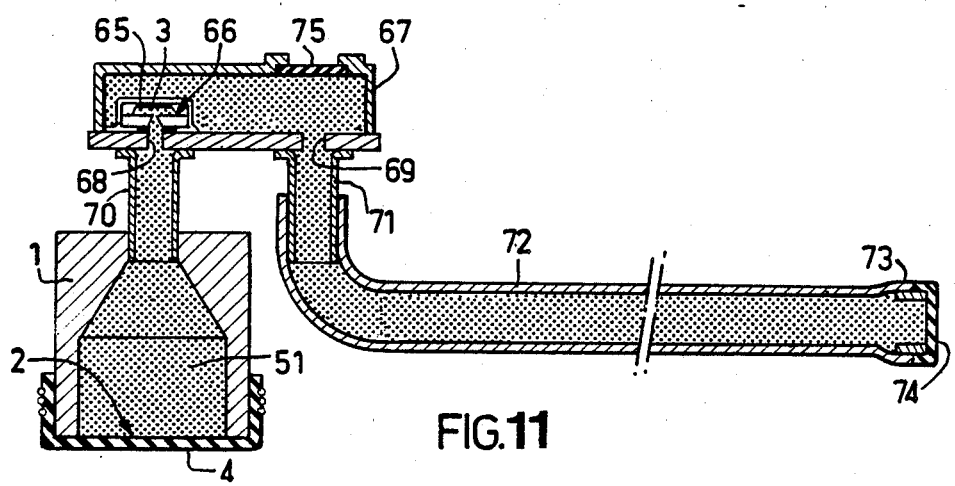
FIG. 11 is a sectional schematic view of a device according to the invention which is of the type comprising a piezo-electric plate associated with elastic deformable means.

Referring now to FIG. 11, an embodiment of the invention is set forth in which a piezo-electric plate is used in such a way that one can pick off a pressure, for example at the wrist, and carry out a precise measurement, no matter what the difference in level between the wrist and the heart is.

The case is shown where the capsule 1 does not contain as intermediate membrane 50, but it could have one in accordance with the indications given above.

More precisely, FIG. 11 shows that the opening 3 of a smaller diameter communicates with a cavity 65 provided in the unit 66 of a known type and comprising a piezo-resistance.

The unit 66 is placed into a box 67 which comprises two extended inputs 68 and 69 at the tips 70 and 71.

The capsule 1 is connected to the tip 70 and enough noncompressible liquid is provided for filling all the space which is limited by the interior of the capsule, the tip 70, the input 68 and the cavity 65.

Over the tip 71 a flexible tube 72 is placed whose end 73 is closed by a membrane 74. A non-compressible liquid is put into the entire space which is limited by the tube 72, the tip 71 and the interior of the box 67.

In this way the piezo-resistance 66 receives on one of its faces the pressure picked off by the membrane 4 and on the other one of its faces a possible pressure existing in the box 67 according to the position of the end 73 of the tube 72.

When the device is used, the membrane 4 is placed onto the desired spot (usually the wrist), and one places the end 73 at the same height as the heart.

In the case of FIG. 11 the membrane 4 is at the same height as the heart. The pick off means connected with the piezoresistance 66 (not shown) thus gives a measurement which corresponds to the real value, with the tube 72 intervening only in a non-effective way.

Figure 12:
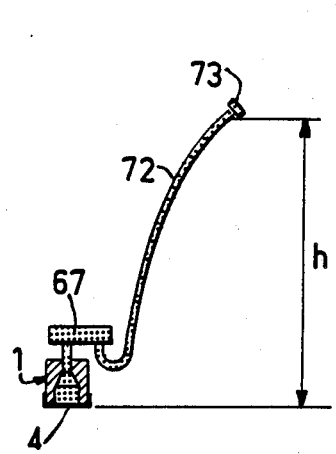

In the case of FIG. 12, the membrane 4 is on a lower level than that of the heart, at a height h. The pick off means indicates the pressure on the membrane 4 minus the pressure of the liquid column contained in the tube 72 and which is the function of the height h.

The piezo-resistance 66 gives in effect the value of the algebraic sum of the two pressures since they are applied onto the two opposite faces of said piezo-resistance 66.

Figure 13:
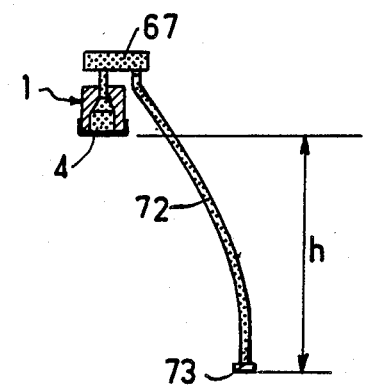

In the case of FIG. 13, the pick off means indicates the pressure on the membrane 4 plus the pressure of the liquid column, because here the membrane 4 is situated higher than the heart (height h).

On the box 67 an opening, closed by an elastic membrane 75, is provided. Its object is to allow the displacement of the piezo-resistance 66 without meeting the resistance which opposes the mass of all the liquid contained in the box 67 and the tube 72, with this liquid being intended only for compensating the natural hydrostatic pressure. It is therefore the object of the membrane 75 to moderate the "work" of the pulse by diminishing the mass of the liquid in movement.

There also exist elastomers whose physical characteristics are more constant in time when utilized in pressure rather than in extension.

One can thus, for having a constant counter pressure, utilize membranes which are made of these materials and which work, as described, not upon extension, but upon pressure.

It is known that the modern materials perform excellently and assure for several years the functioning of membranes which were put in under these conditions of good functioning.

Figure 14:
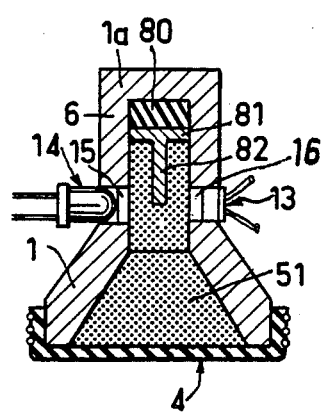
Figure 15:
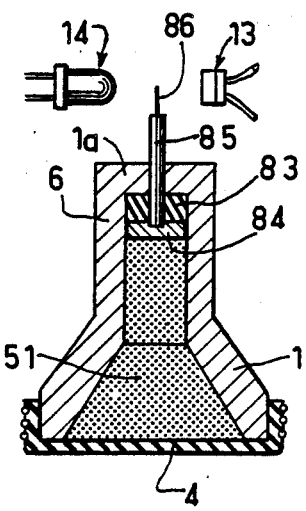

This is the case in FIGS. 14 and 15.

FIG. 14 shows a device analogus to that shown in FIGS. 1 and 2, i.e. of the type according to which the detection of the movement resulting from the deformation of the membrane 4 takes place on the level of the capsule 1 and not above it.

It is therefore not necessary to describe again the optical system 13 - 14 - 15 - 16. It has been chosen to show an embodiment here in which the capsule 1 comprises only a single opening 2.

On the opposite the capsule is closed, and against the bottom 1a an elastic membrane 80 has been placed which is given a cap 81 of the same surface area, carrying a screen 82. The displacement of the screen 82 caused by the pushing against the membrane 80 is analyzed across the non-compressible liquid 51 which is the transmitter of pressure and must be transparent.

FIG. 15 shows a modification which combines the preceding arrangements concerning the membrane working upon compression with the arrangements of FIGS. 1 and 2 relating to the mode of detection.

The capsule 1 has no openings 15 and 16 and the liquid 51 can be opaque. An elastic membrane 83 is compressed by a small, flat piston 84 of the same surface area on which a shaft 85 is mounted which carries the screen 86. The membrane 84 is in fact a small toric joint which is compressed by the pressure exerted upon the piston 84 by the non-compressible liquid 51.

The displacement of the screen 86 is analyzed by a photoelectric cell 13 lighted by a lamp 14.

The optical detection unit is above the capsule 1, with the latter being traversed by a hole through which the shaft 85 passes which carries the screen 86.

Thanks to the invention, dynamic energy of the examined artery is picked off by a simple contact with the skin without strong pressure and, most importantly, without cutting off and clamping the examined artery.

In order to measure the blood pressure, a counter pressure, whose value is known, must exert itself. For this reason, the volume of the non-compressible liquid 5, displaced in the capsule 1 for a variation of the given pressure, must be inferior to the volume available from the surface, perpendicularly to the artery which is examined.

For the application of the invention to the measuring of blood pressure there exists an absolute physical limit: the displacement of the non-compressible liquid cannot be smaller than that of the artery.

The invention is not limited to the embodiments and methods described and shown but includes also all modifications.

I claim:

1. A device for detecting blood pressure through the skin of a patient comprising capsule means defining a chamber having an opening, a flexible membrane extending across and closing said opening, a noncompressible liquid contained in said chamber, solid elastic means positioned opposite said opening to exert a pressure on said noncompressible liquid operating to automatically and instantaneously return said flexible membrane to its rest position when the membrane is momentarily displaced from its rest position, said solid elastic means deforming to a degree varying with the pressure transmitted into said liquid through said membrane means mounting said capsule to enable said membrane to be applied directly against the skin of a patient from which a pressure is to be detected, said membrane comprising a flexible sheet adapted and arranged to conform to the shape of and lie flat against the skin of a patient, said opening being large enough to transmit blood pressure through the skin of a patient, and said membrane into said liquid, and means to detect the degree of deformation of said solid elastic means in response to variations in pressure applied to said noncompressible liquid and to indicate the blood pressure of the patient.

2. A device according to claim 1, wherein said chamber has a second opening smaller than said first mentioned opening, positioned opposite said first mentioned opening, and further comprising means closing said second opening, said second opening closing means not being removeable from said second opening in normal service.

3. A device according to claim 2, wherein said chamber includes a neck portion of smaller diameter than the remainder of said chamber.

4. A device according to claim 1, wherein said elastic means comprises a second membrane and a spring positioned to apply a force against said second membrane.

5. A device as recited in claim 1, wherein said detector comprises a photoelectric cell and projector means to direct a light beam through said chamber towards said photoelectric cell.

6. A device as recited in claim 1, wherein said detecting means comprises a photoelectric cell, means to direct a light beam toward said photoelectric cell, a moveable screen positioned between said projector means and said photoelectric cell and means to move said moveable screen in accordance with the pressure applied to said noncompressible liquid in said chamber.

7. A device according to claim 6, wherein said screen comprises one end of a flexible blade, means mounting the other end of said flexible blade in a fixed position relative to said capsule means and wherein said means to move said screen comprises means to deflect said flexible blade in accordance with the pressure in said chamber.

8. A device according to claim 1, wherein rigid circular bands sandwich the edges of said membrane between said bands and said capsule means to mount said membrane on said capsule means.

9. A device according to claim 1, wherein said means to detect the degree of deformation of said solid elastic means comprising a transducer for generating an electrical signal varying in accordance with the displacement of said liquid in said chamber.

10. A device according to claim 1, further comprising means defining a surface for receiving an applied counter pressure at a location different than said membrane and means to detect the algebraic sum of the pressure applied through said membrane and said counter pressure.

11. A device according to claim 1, further comprising a detector to detect the level of said noncompressible liquid in said chamber.

12. A device as recited in claim 11, wherein said detector comprises means to optically detect the level of noncompressible liquid in said chamber.

13. A device according to claim 1, wherein a transverse deformable membrane is provided in said chamber fixed at its periphery to the walls of said chamber to divide said chamber into two isolated portions, one of said portions having said opening and being filled with noncompressible liquid and the other of said portions containing noncompressible liquid.

14. A device according to claim 13, wherein said chamber has a curved wall shaped to conform to the shape to which said transverse deformable membrane deforms when it undergoes maximum deformation, so that said membrane is supported by said curved wall.

15. A device according to claim 14, wherein said curved wall defines a spherical surface.

16. A device according to claim 1, wherein said means to exert a calibrated pressure on said liquid comprises a compressible membrane positioned in said chamber to be compressed by said liquid as the pressure in said liquid increases, and wherein said device further comprises a screen in said chamber immersed in said liquid, means mounting said screen to be moved with compression of said compressible membrane, and means to detect the position of said screen in said liquid.

17. A device according to claim 1, wherein said means for exerting an invariable calibrated pressure on said liquid comprises a compressible membrane in said chamber, and a piston in said chamber between said liquid and said compressible membrane and movable by said liquid to compress said compressible membrane, said device further comprising a screen outside of said chamber and a rod connecting said piston to said screen to be moved with said piston, and means to detect the position of said screen.

* * * * *